United States Patent
Lavore

[19]

[11] Patent Number: 5,837,004
[45] Date of Patent: Nov. 17, 1998

[54] DEVICE FOR TREATMENT OF TEMPOROMANDIBULAR JOINT DYSFUNCTION

[76] Inventor: Joseph S. Lavore, 6492 Sugar Tree Dr., Spring Hill, Fla. 34607

[21] Appl. No.: 819,784

[22] Filed: Mar. 18, 1997

[51] Int. Cl.$^6$ ........................................................ A61F 7/00
[52] U.S. Cl. ............................ 607/109; 607/112; 607/114
[58] Field of Search ..................................... 607/108, 112, 607/114; 165/46; 126/204

[56] References Cited

U.S. PATENT DOCUMENTS

| | | | |
|---|---|---|---|
| 1,567,931 | 12/1925 | Epler | 607/109 X |
| 3,889,684 | 6/1975 | Lebold | 607/108 X |
| 4,552,149 | 11/1985 | Tatsuki | 607/109 X |
| 4,756,311 | 7/1988 | Francis, Jr. | 607/114 |
| 4,805,620 | 2/1989 | Meistrell | 607/108 X |
| 5,020,536 | 6/1991 | Keen | 607/109 |
| 5,188,103 | 2/1993 | Smith | 607/109 |
| 5,456,703 | 10/1995 | Beeuwkes, III | 607/109 X |

*Primary Examiner*—Jeffrey R. Jastrzab
*Assistant Examiner*—Ryan Carter
*Attorney, Agent, or Firm*—Dorothy S. Morse

[57] ABSTRACT

A device to reduce pain, relax muscle spasm, decrease swelling, and increase circulation to the bones, joints, and muscles of the face of a patient having temporomandibular joint dysfunction, the device having a thin, hexagonal configuration with an essentially uniform cross-section, and a flexible outer envelope having a perimeter limited to covering an area on one side of a patient's face to minimally include the area over the rear portion of the patient's mandible, the zygomatic arch, the front portion of the temporal bone, the great wing of the sphenoid bone, the lower front portion of the parietal bone, the outer envelope also having hook material on both sides of the upper panel placed away from the patient's face so that it can also be used inside-out against the opposite side of the patient's face and the lower rear portion of the frontal bone. Also the outer envelope is secured to the treated area by a separate quick-release non-stretchable strap comprising pile material on one of its sides, and the outer envelope has a removable inner member comprising a gel that can be heated and chilled, without hardening. Applications of the present invention, although not limited to the minimizing of pain, muscle spasms, and inflammation of joints associated with temporomandibular joint dysfunction are best suited for such purposes since its perimeter closely approximates the area on a patient's face which contains pain sensitive structures most commonly affected by temporomandibular joint dysfunction.

18 Claims, 1 Drawing Sheet

DEVICE FOR TREATMENT OF TEMPOROMANDIBULAR JOINT DYSFUNCTION

BACKGROUND - FIELD OF INVENTION

This invention relates to heat releasing and heat absorbing therapeutic treatment pads, specifically to a device to reduce pain, relax muscle spasm, decrease swelling, and increase circulation to the bones, joints, and muscles on one side of the face of a patient having temporomandibular joint dysfunction, the device having a flexible outer envelope with a hexagonal configuration of sufficient dimension to minimally cover a treatment area extending over the rear portion of the mandible, the patient's zygomatic arch, the front portion of the temporal bone, the great wing of the sphenoid bone, the lower front portion of the parietal bone, and the lower rear portion of the frontal bone, the device further comprising thermal means within its outer envelope for both chilling and heating the treated area and being secured to the treated area by at least one quick-release strap. Applications of the present invention, although not limited to the minimizing of pain, muscle spasms, and inflammation of joints associated with temporomandibular joint dysfunction, are best suited for such purposes since it is dimensioned to optimally, but minimally, cover the area on a patient's face which contains pain sensitive structures most commonly affected by temporomandibular joint dysfunction.

BACKGROUND - DESCRIPTION OF PRIOR ART

Temporomandibular joint dysfunction has many causes, including arthritis, accidents, oral habits such as teeth clenching, and malocclusion. The symptoms include muscle spasm, limitation of motion, ear aches, jaw clicking, crepitation, dislocation, locking, tinnitus, hearing loss, bruxism, dizziness, toothache, and other types of chronic craniofacial pain. Also, when a patient experiences temporomandibular joint dysfunction on one side of his or her face, the patient can experience symptoms of temporomandibular joint dysfunction on the other side of his or her face. While physical therapy can relieve some of the symptoms of temporomandibular joint dysfunction application of heat to the temporomandibular area of the skull can also provide some sufferers with temporary relief from chronic pain. Further, when cold is applied to the temporomandibular area within the first seventy-two hours after the on-set of temporomandibular joint dysfunction symptoms, such cold can provide sufferers relief from both pain and swelling. For convenience of use it would be most desirable to have one device for the alternate application of both heat and cold, as well as one device for optimally treating both sides of the patient's face.

However, since the skin over the temporomandibular area can become extremely sensitive to pressure during temporomandibular joint dysfunction, known prior art devices and methods are unsuitable for applying both heat and cold to the temporomandibular area. They are either too large, too heavy, have compressing components which apply too much pressure, to the patient's skin or are otherwise inappropriate for use against the extremely pressure-sensitive skin of a temporomandibular joint dysfunction patient. It is not known to have a compact, thinly-profiled, lightweight, hexagonally shaped device, having a flexible outer envelope specifically configured to optimally, but minimally, lay flat against the area of a patient's face most commonly affected by temporomandibular joint dysfunction, the outer envelope having a removable inner member made of non-hardening gel to facilitate the alternative application of both heat and cold to the temporomandibular area of the patient's skull.

There are many known therapeutic devices for applying heat and cold to different parts of a human body. For example, the devices in U.S. Pat. No. 3,889,684 to Lebold (1975) and U.S. Pat. No. 4,891,501 to Lipton (1990) each disclose a flexible envelope into which a heating or cooling element can be placed. The preferred embodiment of the Lebold invention is essentially rectangular with its top and sides detachably fastened to enclose the envelope. In contrast, the Lipton invention has an elongated configuration with a centrally located semi-circular cut-out along one edge. However, neither teaches a hexagonal envelope configured for optimal coverage over the area of a patient's face most likely affected by temporomandibular joint dysfunction. Although the Lebold and Lipton inventions are both useful for the application of heat and cold to various parts of the body, neither is suitable for temporomandibular joint dysfunction use as they are not compactly shaped to cover only the temporomandibular joint and as a result each would be too heavy and they apply too much pressure to the ultra-sensitive skin of temporomandibular joint dysfunction patients.

Therapeutic devices which apply both heat and cold to specific areas on a patient's body through the use of compression bandages, are also inappropriate for use in treating temporomandibular joint dysfunction as they would apply too much pressure to the ultra-sensitive skin of a temporomandibular joint dysfunction patient. Two such compression devices are disclosed in U.S. Pat. No. 5,188,103 to Smith (1993) and U.S. Pat. No. 4,190,054 to Brennan (1980). The Smith invention discloses an adjustable main elastic band encircling a patient's head, face, or neck, to which thermal pouches can be attached in various locations thereon with hook-and-pile fasteners. Hooking tape tabs engage opposite sides of the main elastic band to anchor it securely in place during use. Similarly, the Brennan invention comprises a removable elastic bandage configured for attachment to specific body parts, including the head and neck of a patient. The Brennan invention contemplates envelopes containing hot and cold liquid to be attached with hook-and-pile fasteners to various pre-selected areas on the outside of its bandage. The Brennan elastic bandage and the Smith compression device would both apply uncomfortable pressure to inflamed temporomandibular joints and would be inappropriate for treatment thereof. Further, the present invention is dissimilar from the Brennan invention in that the present invention is configured to evenly apply heat or cold to the entire temporomandibular treatment area at once, while the Brennan invention cannot.

Other thermal therapeutic devices comprising an outer envelope and means placed therein to apply heat or cold to the head or neck of a patient are disclosed in U.S. Pat. No. 5,400,617 to Ragonesi (1995), U.S. Pat. No. 5,119,812 to Angelo (1992), U.S. Pat. No. 4,641,655 to Abt (1987), and U.S. Pat. No. 5,247,928 to Stilts, Jr. (1993). The Ragonesi invention discloses an elongated sheath that can be folded in half longitudinally, with its edges sealed together through the use of adhesive strips or zippers, to contain a cooling means. Also, contained within the sheath is a flexible leaf which when bent causes the sheath to conform to the shape of a body part for which cooling is desired. The present invention differs from the Ragonesi invention in that the present invention is compactly configured for specific use in the temporomandibular joint area of a face and to avoid treatment of unnecessary areas. In contrast, the Angelo invention comprises at least three individual sections, for individual or collective use, each section being specifically configured for use with either the upper, middle, or lower portion of a patient's face. Each section of the Angelo invention wraps laterally around both sides of a patient's face, while the present invention is configured for secure attachment against a specific treatment area on one side of a patient's face. Further, the Angelo invention differs from the present invention as its thermal storage substance is not removable from its outer layers, nor are its straps removably attachable to different portions of its sections for maximum contact of its thermal storage substance against a treatment area while avoiding the application of uncomfortable pressure to the treatment area.

The Abt invention differs from the present invention in that the Abt invention comprises an elongated wrap for attachment around the neck of a person vigorously exercising, the ends of the wrap forming tying straps and the center portion of the wrap having a pouch into which a frozen water medium, such as ice cubes or crushed ice, can be placed. The Abt invention would be bulky and thereby would inappropriately apply uncomfortable pressure to the treatment area of a temporomandibular joint dysfunction sufferer. Also, the use of crushed ice would make the Abt invention hard and therefore not ideally suited for the treatment of temporomandibular joint dysfunction. Further, the Abt invention is distinguished from the present invention as the configuration of the Abt invention does not completely cover the entire treatment area required for relief of temporomandibular joint dysfunction symptoms. The Stilts, Jr. invention provides an elongated therapeutic collar of soft material which has an inner compartment for containment of a coolant material such as crushed ice or a chemical material which induces heat. The Stilts, Jr. invention has a spout for filling the inner compartment and a flap extending over an access port to its inner compartment. The present invention differs from the Stilts, Jr. invention in that the present invention has no spout for filling a inner compartment as its thermal substance is in the form of a convenient-to-use, thinly-profiled, sealed gel pack. Also, the Stilts, Jr. invention would be cumbersome to use against the treatment area of a person suffering from temporomandibular joint dysfunction, thereby contributing to the person's pain instead of relieving it.

The prior art thought to be most closely related in configuration to the present invention are the inventions disclosed in U.S. Pat. No. 5,020,536 to Keen (1991) and U.S. Pat. No. 5,514,170 to Mauch (1996). However, both the Keen and Mauch inventions are contemplated only for cryokinetic therapy and neither has the hexagonal shape of the present invention. The Keen invention comprises a postoperative device comprising two vertical straps and one horizontal strap, all of which can be adjustably positioned around a patient's head with hook-and-pile fasteners. Pouches attached to the vertical straps are configured for receiving sealed containers of ice for cryokinetic therapy. In contrast, the Mauch invention comprises a housing with an insulating member and a resilient inner member which has an opening therethrough that allows insertion of a cold pack. A cover over the opening allows the Mauch invention to adapt to body contours. Straps attached to opposite sides of the housing attach it around a selected body part of a patient. The cold packs for retaining ice that are secured by the Keen invention against the face of a patient are bulky as compared to the present invention and thereby would apply uncomfortable pressure against a temporomandibular joint dysfunction treatment area. It is not known in this field to have a device for applying both heat and cold to soothe and relax the bones, joints, and muscles of the face of a patient having temporomandibular joint dysfunction which has a hexagonal configuration that is not cumbersome and avoids applying uncomfortable pressure to any portion of the treated area on a patient's face during use, the device having a dimension limited to covering a treatment area on one side of a patient's face laterally extending between the front part of the patient's ear and the outer corner of the patient's eye, also laterally extending between the outer portion of the patient's chin and the lower rear portion of the patient's jaw, and extending vertically between the patient's upper temple and the lowest extent of the patient's jaw, to include at a minimum the skin area over the rear portion of the mandible, the zygomatic arch, the front portion of the temporal bone, the great wing of the sphenoid bone, the lower front portion of the parietal bone, and the lower rear portion of the frontal bone.

SUMMARY OF INVENTION - OBJECTS AND ADVANTAGES

It is the primary object of this invention to provide a treatment device for the area of a human face subjected to temporomandibular joint dysfunction pain and swelling. It is also an object of this invention to provide a treatment device for temporomandibular joint dysfunction which can be both heated in a microwave oven and chilled in a freezer. A further object of this invention is to provide a treatment device for temporomandibular joint dysfunction which can be chilled without hardening. It is also an object of this invention to provide a treatment device for temporomandibular joint dysfunction which has a thin profile and a compact configuration so as not to produce uncomfortable pressure against the treatment area and which avoids treatment of unnecessary areas of the face.

As described herein, properly manufactured and positioned against the temporomandibular area of a human face, the present invention would provide a comfortable, easy-to-use treatment device for soothing and relaxing the bones, joints, and muscles of the face of a patient having temporomandibular joint dysfunction. The specific configuration of its flexible outer envelope, with its hexagonal perimeter having a first short upper side for extending across the upper part of a patient's temple, a second side extending between one end of the first side and the outer corner of the patient's eye, a third side extending between the outer corner of the patient's eye and the outside part of the patient's chin, a fourth short lower side approximately parallel to the first side for extending between the outside part of the patient's chin and the middle part of his or her jaw bone, a fifth side extending between one end of the fourth side and the lower rearmost portion of the patient's jaw bone, and a sixth arcuate side extending in front of the patient's ear between the fifth and first sides, to include at a minimum the skin area over the rear portion of the mandible, the zygomatic arch, the front portion of the temporal bone, the great wing of the sphenoid bone, the lower front portion of the parietal bone, and the lower rear portion of the frontal bone, provides adequate contact with the entire area of a patient's face affected by temporomandibular joint dysfunction while at the same time avoiding other facial areas not requiring treatment to provide a less bulky thermal treatment device than prior art devices, but one that is effective. In embodiments having hooking material substantially covering the panel of its outer envelope intended for placement away from a patient's face, the present invention provides a means for comfortable attachment of the pile material on the invention's strap in a variety of positions. The thin profile of the present invention allows it to lay flat against the entire treatment area to evenly apply pressure thermal distribution throughout the treatment area, and the slit in the back of the envelope fabric allows a heated or chilled gel pack to be easily inserted and removed from the outer envelope. Since the gel pack comprises material capable of being both heated and chilled, and since it can become chilled without hardening, the present invention provides a convenient-to-use, versatile means for treating adverse symptoms associated with temporomandibular joint dysfunction. Also in the preferred embodiment of the outer envelope having hook material on opposed sides of the one of its surfaces intended for placement away from the patient's face and a slit through the back of the envelope fabric, the outer envelope can be used to treat one side of a patient's face, then easily turned inside-out for use in providing a device for treating the temporomandibular area on the opposite side of the patient's face The description herein provides preferred embodiments of the present invention but should not be construed as limiting the scope of the temporomandibular joint treatment device invention. For example, variations in length of the strap, the number of straps used, the dimension and configuration of the hooking material on the top surface of the outer envelope, the amount of pile material on each strap, the length of the back slit, the amount of non-hooking material on the front portion of the outer envelope, and the type of gel used in the gel pack provided for insertion into the outer envelope, other than those shown and described herein, may be incorporated into the present invention. Thus the scope of the present invention should be determined by the appended claims and their legal equivalents, rather than the examples given.

DETAILED DESCRIPTION OF PREFERRED EMBODIMENTS

Figure 1:
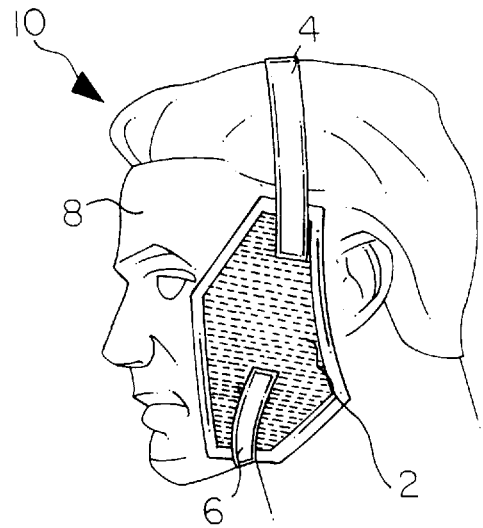
FIG. 1 is a side view of the invention attached to the temporomandibular treatment area of a human face.

FIG. 1 shows a preferred embodiment of a temporomandibular treatment device 10 positioned over the temporomandibular treatment area on one side of a human face 8 and comprising an outer envelope 2 having a configuration laterally extending between the front part of the patient's ear and the outer corner of the patient's eye, also laterally extending between the outer portion of the patient's chin and the lower rear portion of the patient's jaw, and extending vertically between the upper portion of the patient's temple and the lowest extent of the patient's jaw. Although not shown, such a configuration would cover the skin area over the rear portion of the mandible, the zygomatic arch, the front portion of the temporal bone, the great wing of the sphenoid bone, the lower front portion of the parietal bone, and the lower rear portion of the frontal bone. FIG. 1 also shows outer envelope 2 being secured to the treated area by a quick release strap having an upper portion 4 and lower portion 6. It is contemplated for the strap to be made of non-stretchable material so that unnecessary pressure to the treatment area is avoided. In the preferred embodiment is contemplated for the top surface of outer envelope 2 to have hooking material substantially covering it, shown in FIG. 4 as number 12, and for the underside surface of upper portion 4 and lower portion 6 to comprise pile material 20 so that hooking material 12 and pile material 20 in combination securely fix the strap to the top surface of outer envelope 2 during use, and so that the strap can be quickly released from outer envelope 2 after use. Since outer envelope 2 is configured to conform to a specific area on one side of face 8, either two temporomandibular treatment devices 10, each the mirror image of the other, would be used to treat opposite sides of face 8, or outer envelope 2 could be made reversible so that fabric 16, shown in FIG. 2, could be turned inside-out for such use. Simultaneous temporomandibular joint dysfunction on both sides of face 8 is common. Therefore, it is also contemplated for two temporomandibular treatment devices 10 to be used simultaneously, when needed, to treat opposite sides of face 8.

Figure 2:
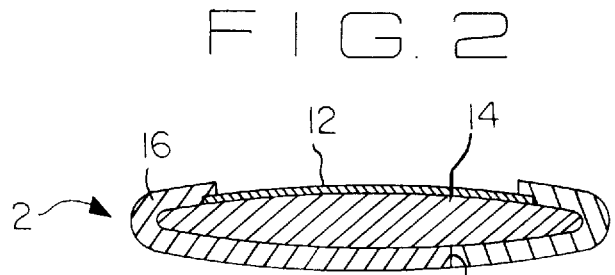
FIG. 2 is a sectional side view of the invention taken from line 2—2 in FIG. 5 and having a gel pack positioned within an outer envelope.
Figure 3:
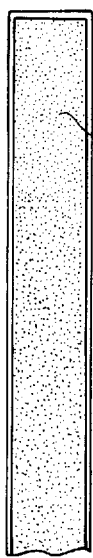
FIG. 3 is a bottom view of the strap of the invention.
Figures 4, 5:
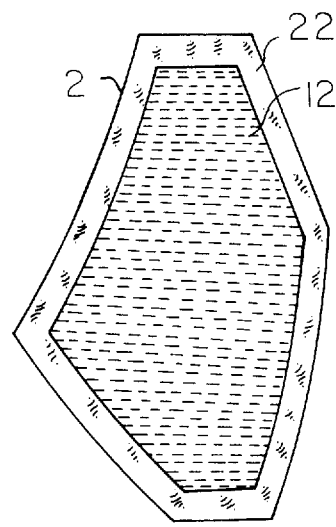
FIG. 4 is a top view of the outer envelope of the invention.
FIG. 5 is a back view of the outer envelope of the invention.

FIG. 2 shows outer envelope 2 having fabric 16 forming its back portion, shown in FIG. 5 as number 24. FIG. 2 also shows an access slit 18 through fabric 16. Although not critical to the present invention, in the preferred embodiment it is contemplated for access slit 18 to be vertically positioned through the back of fabric 16. FIG. 2 further shows fabric 16 forming a portion of the front surface of outer envelope 2 and connected to a piece of hooking material 12, fabric 16 and hooking material 12 in combination forming the front portion of outer envelope 2. In addition, FIG. 2 shows a gel pack 14 positioned between fabric 16 and hooking material 12, substantially filling and being totally contained within outer envelope 2. FIG. 2 also shows outer envelope 2 having a thin, cross-sectional configuration that is substantially uniform in width. In the preferred embodiment it is contemplated for fabric 16 to be flexible, easily washable, and soft to the touch. Fabric 16 can also comprise any combination of colors and decorative designs to make outer envelope 2 more attractive for use. It is also contemplated for hooking material 12 to have hooking members of sufficient dimension, number, and size for use with pile material, shown in FIG. 3 as number 20, so that hooking material 12 and pile material 20 together form a quickly releasably but securely fastened bond when in contact with one another. It is further contemplated for gel pack 14 to be made of a gel material that can be easily and quickly heated in a microwave oven or chilled in a freezer without hardening. Also, the gel material used should maintain the hot and cold temperatures for extended periods of time. Access slit 18 must also be of sufficient size and dimension for gel pack 14 to be easily inserted and removed from envelope 2. Although not shown, it is contemplated for hooking material 12 to be attached to fabric 16 by conventional means, such as stitching, and for the portion of fabric 16 adjacent to access slit 18 to be secured to prevent raveling, again by stitching or other conventional means.

FIG. 3 shows upper portion 4 of the strap having pile material 20 attached to its underside surface. Neither the length of upper portion 4, nor the amount of pile material 20 used, is critical to the present invention as long as sufficient pile material 20 is present to securely fasten upper portion 4 to hooking material 12 during use in positioning outer envelope 2 against the temporomandibular area of face 8. Although not shown, it is contemplated for lower portion 6 of the strap to be configured similarly with pile material 20 on its underside surface. Neither the length of lower portion 6, nor the amount of pile material 20 used, is critical to the present invention as long as sufficient pile material 20 is present to securely fasten lower portion 6 to hooking material 12 during use in securing outer envelope 2 comfortably against the temporomandibular area of face 8. Also, although not shown, it is contemplated for more than one strap to be used to attach outer envelope 2 comfortably against the temporomandibular area of face 8. Also, the widths, as well as the thicknesses, of upper portion 4 and lower portion 6 are not critical to the present invention, nor are the means of attachment of pile material 20 to upper portion 4 and lower portion 6. In the preferred embodiment it is contemplated for pile material 20 to be attached to upper portion 4 and lower portion 6 by stitching (not shown).

FIGS. 4 and 5 show the configuration which outer envelope 2 must have to substantially and effectively cover the area required for treatment of temporomandibular joint dysfunction. FIG. 4 shows fabric 16 around the perimeter of front side 22, with a wide area of hooking material 12 positioned centrally on its front side 22 and a border of fabric 16 positioned around the outer edge of hooking material 12. FIG. 5 shows access slit 18 positioned through the back side 24 of outer envelope 2. The length of access slit 18 is not critical to the preferred embodiment of the present invention as long as gel pack 14 can be easily inserted therethrough when placed into and removed from outer envelope 2. Not critical to the present invention are the length of the straps used, the exact dimension and configuration of hooking material 12 positioned on the top surface of outer envelope 2 as long as hooking material 12 provides adequate variation in angles of attachment of upper portion 4 and lower portion 6 to provide maximum comfort of the patient in positioning outer envelope 2 against the temporomandibular joint dysfunction treatment area of face 8. Also, not critical to the present invention are the amount of non-hooking material on the front portion of the outer envelope and the type of gel used in gel pack 14.

To use the preferred embodiment of temporomandibular treatment device 10, one would first remove gel pack 14 from its position within outer envelope 2. Gel pack 14 would be placed into a microwave oven (not shown) to heat it, or into a freezer (not shown) to chill it. When sufficiently hot or cold, gel pack 14 would be re-inserted through access slit 18 and positioned within outer envelope 2 to substantially fill outer envelope 2. Outer envelope 2 would then be placed against the treatment area on face 8 so that hooking fabric 12 is remotely positioned from the skin on face 8. Then pile material 20 on the strap's lower portion 6 would be securely connected to hooking material 12. Lower portion 6 would then be brought under the patient's chin so that the remainder of the strap can be brought around the patient's head for connection of the pile material 20 on the strap's upper portion 4 to an upper part of hooking material 12. Due to the configuration of outer envelope 2, areas on face 8 not requiring treatment are avoided. This makes the present invention less bulky and avoids uncomfortable pressure from being applied to the treatment area on face 8. Since the present invention is thinly profiled and compact in shape, pressure is evenly distributed over the entire treatment area to provide additional comfort to a user. Also, the compact shape allows a user to easily take the present invention to work in a briefcase or purse. The present invention could be conveniently used in a workplace as it can be quickly heated in a microwave oven (not shown), or chilled in a freezer (not shown), both appliances being commonly available in workplaces. Since outer envelope 2 does not require filling with crushed ice or cold water, the present invention is simpler to use in the workplace than many prior art thermal treatment devices. It is also less bulky and more thereby more comfortable for use by temporomandibular joint dysfunction sufferers. Since outer envelope 2 can be made from any soft, attractive fabric 16, and since it has a compact and minimal shape, the present invention is not unattractive and can be confidently worn in the workplace.

What is claimed is:

1. A treatment device for soothing and relaxing the bones, joints, and muscles one side of the face of a patient having temporomandibular joint dysfunction which typically affects a facial area in front of said patient's ear covering the rear portion of said patient's mandible, the zygomatic arch, the front portion of the temporal bone, the great wing of the sphenoid bone, the lower front portion of the parietal bone, and the lower rear portion of the frontal bone, said device comprising a flexible outer envelope having a hexagonal configuration of sufficient size to minimally cover said facial area; non-stretchable strap means for attaching said outer envelope against said facial area of said patient during treatment use; fastening means connected to said strap means and said outer envelope to attach said strap means to said outer envelope during use; and thermal means within said outer envelope for both chilling and heating said facial area, said thermal means being able to remain heated and chilled for extended periods of time, and able to become chilled without hardening; and wherein said fastening means further comprises said outer envelope having a top panel with an outside surface intended for placement away from said facial area, and said outside surface of said top panel substantially comprising hooking material; and wherein said fastening means also comprises said strap means having a sufficient quantity of pile material configured for secure connection to said hooking material so that said strap means can be releasably attached to said outer envelope to position said outer envelope comfortably against said facial area of said patient; and further wherein said outer envelope further comprises a bottom panel having an outside surface intended for placement against said facial area and said outside surface of said bottom panel substantially comprising soft material, wherein said top panel and said bottom panel each comprise an inside surface, said inside surface of said top panel substantially comprising hooking material, and said inside surface of said bottom panel substantially comprising soft material, and further wherein said bottom panel comprises an access slit therethrough to facilitate turning said outer envelope inside-out to create a configuration suitable for treating the bones, joints, and muscles on the opposite side of said patient's face.

2. The device of claim 1 wherein said outer envelope further comprises a thin cross-sectional configuration of substantially uniform depth for even contact of said outer envelope against said facial area and even distribution of heat and cold thereto.

3. The device of claim 1 wherein said outer envelope is made from washable material.

4. The device of claim 1 wherein said thermal means comprises materials which can be heated in a microwave oven and chilled in a freezer without rupture.

5. The device of claim 1 wherein said hexagonal configuration of said outer envelope comprises the shape of an irregular hexagon with one concavely arcuate side suitably configured for placement in front of said patient's ear during treatment use so to provide flat contact of said outer envelope against said entire facial area for enhanced even distribution of heat and cold thereto.

6. A treatment device for use by a patient suffering from temporomandibular joint dysfunction and adapted to evenly apply both heat and cold to a facial area on one side of a patient's face most likely affected by temporomandibular joint dysfunction which extends between the outer corner of said patient's eye, the outside part of said patient's chin, the center portion of said patient's jaw bone, the rearmost portion of said patient's jaw bone, said patient's ear, and the upper portion of said patient's temple, said device comprising a flexible outer envelope; an inner member configured for placement within said outer envelope, which substantially fills said outer envelope, and which can be repeatedly heated and chilled; non-stretchable quick-release strap means adapted to attach said outer envelope to said facial area; and fastening means connected to said strap means and said outer envelope adapted to attach said outer envelope against said facial area during use; and wherein said device further comprises said outer envelope having a closed perimeter with six sides and a surface area adapted to minimally cover said facial area, each of said sides having opposite ends, the first one of said sides having a short length dimension adapted for extending across said upper portion of said patient's temple, a second one of said sides adapted for extending between one of said opposite ends of said first side and said outer corner of said patient's eye, a third one of said sides adapted for extending between the other of said opposite ends of said second side and said outside part of said patient's chin, a fourth one of said sides having a short length dimension substantially equivalent to said short length dimension of said first side adapted for extending between the other of said opposite ends of said third side and said center portion of said patient's jaw bone, said fourth side also being approximately parallel to said first side, a fifth one of said sides adapted for extending between the other of said opposite ends of said fourth side and said rearmost portion of said patient's jaw bone, and a sixth one of said sides adapted for extending in front of said patient's ear between the other of said opposite ends of said fifth and said first sides.

7. The device of claim 6 wherein said outer envelope has a thin depth of approximately uniform dimension throughout for even distribution of said heat and said cold to said facial area.

8. The device of claim 6 wherein said fastening means further comprises said outer envelope having a top panel with an outside surface intended for placement away from said facial area, and said outside surface of said top panel substantially comprising hooking material; and wherein said fastening means also comprises said strap means having a sufficient quantity of pile material configured for secure connection to said hooking material so that said strap means can be releasably attached to said outer envelope to position said outer envelope comfortably against said facial area of said patient.

9. The device of claim 8 wherein said outer envelope further comprises a bottom panel having an outside surface intended for placement against said facial area and said outside surface substantially comprising soft material, wherein said top panel and said bottom panel each comprise an inside surface, said inside surface of said top panel substantially comprising hooking material, and said inside surface of said bottom panel substantially comprising soft material, and further wherein said bottom panel comprises an access slit therethrough to facilitate turning said outer envelope inside-out to create a configuration suitable for treating the bones, joints, and muscles on the opposite side of said patient's face, said access slit also configured for allowing easy insertion and removal of said inner member from said outer envelope.

10. The device of claim 9 wherein said slit extends longitudinally between the approximate intersection of said sixth side with said first side and the approximate intersection of said fourth side with said fifth side.

11. The device of claim 6 wherein said sixth side is concavely arcuate for optimum placement of said outer envelope in front of said patient's ear during use to allow for flat contact of said outer envelope against said entire facial area for enhanced even distribution of heat and cold thereto.

12. The device of claim 6 wherein said inner member comprises a gel which will not harden when chilled and which is slow to dissipate and absorb heat so that said gel will remain heated and chilled for extended periods of time.

13. The device of claim 6 wherein said inner member is configured to withstand heating in a microwave oven and chilling in a freezer without rupture.

14. The device of claim 6 wherein said outer envelope comprises washable materials.

15. A method for treating temporomandibular joint dysfunction, wherein said method comprises the steps of providing a patient having temporomandibular joint dysfunction, a quantity of soft flexible material, a quantity of flexible hook material having hooking members on both sides, a quantity of non-stretchable pile material, and an inner member comprising non-hardening gel which can be both heated and chilled without rupture; cutting said quantity of soft flexible material to form a hexagon having a first upper side of a short length dimension for placement across the patient's upper temple, a second side contiguous with said first side and having a length dimension sufficient to extend between said upper temple and the outer corner of one of the patient's eyes, a third side contiguous with said second side and having a length dimension sufficient to extend between said outer corner of said patient's eye and the outer portion of said patient's chin, a fourth side contiguous with said third side and having a length dimension sufficient to extend between said outer portion of said patient's chin and the middle portion of said patient's jaw bone, while also making said fourth side approximately equal in length to said first side and approximately parallel thereto, a fifth side contiguous with said fourth side and having a length dimension sufficient to extend between said middle portion of said patient's jaw bone and the rearmost portion of said jaw bone, a sixth side contiguous with said fifth and first sides; making an approximately straight access slit through said soft flexible material longitudinally between said first and said fourth sides and of sufficient size to easily move said inner member therethrough; cutting said quantity of hook material to form a configuration identical to said hexagon cut from said soft flexible material; aligning said hexagons so that said first side and said sixth side of said hexagon cut from said soft, flexible material is placed against said first side and said sixth side of said hexagon cut from said hook material; connecting said hook material to said soft flexible material to form an outer envelope of approximately uniform depth dimension; forming said inner member into a hexagonal configuration sufficient for substantially filling said outer envelope; altering the temperature of said inner member from the body temperature of said patient; placing said inner member through said slit and into said outer envelope; placing said outer envelope gently against said patient's face so that said sixth side is adjacent to said patient's ear; cutting said quantity of pile material to form an elongated strap; positioning one end of said strap across said first side of said outer envelope and at the same time attaching said pile material on said strap to said hook material; positioning the other end of said strap across said fourth side of said outer envelope and at the same time attaching said pile material on said strap to said hook material so that said outer envelope is gently and comfortably in contact with said patient's face; and thereafter treating the other side of said patient's face by disengaging said strap ends from said hooking material, removing said inner member from said outer envelope, using said access slit to turn said outer envelope inside-out, replacing said inner member within said outer envelope, repositioning said outer envelope against said face of said patient, reattaching one end of said strap to said hook material across said first side of said outer envelope; and reattaching the other end of said strap to said hook material across said fourth side of said outer envelope to comfortably and gently position said outer envelope against the other side of said patient's face.

16. The method of claim 15 wherein said step of providing said outer envelope further comprises the step of providing an outer envelope having a sixth side which is concavely arcuate for placement in front of said patient's ear and enhanced even distribution of heat and cold to said patient's face.

17. The method of claim 15 wherein said step of providing said soft flexible fabric further comprises the step of providing a quantity of soft flexible material which is washable.

18. The method of claim 15 wherein said step of providing said inner member further comprises the step of providing an inner member configured to withstand heating in a microwave oven and chilling in a freezer without rupture.

* * * * *